(12) United States Patent
Kim et al.

(10) Patent No.: US 11,236,343 B2
(45) Date of Patent: Feb. 1, 2022

(54) METHOD FOR PRODUCING DEXTRAN POLYMER-BASED, AMPLIFIED NUCLEIC ACID APTAMER NANOCONSTRUCT SELECTIVELY CAPTURING TARGET MOLECULE

(71) Applicants: INSTITUTE FOR BASIC SCIENCE, Daejeon (KR); POSTECH ACADEMY-INDUSTRY FOUNDATION, Pohang-si (KR)

(72) Inventors: Won Jong Kim, Pohang-si (KR); Jeong Hun Kim, Seoul (KR); Jihyun Lee, Pohang-si (KR); Byung Joo Lee, Seoul (KR)

(73) Assignees: INSTITUTE FOR BASIC SCIENCE, Daejeon (KR); POSTECH ACADEMY-INDUSTRY FOUNDATION, Pohang-si (KR)

( * ) Notice: Subject to any disclaimer, the term of this patent is extended or adjusted under 35 U.S.C. 154(b) by 378 days.

(21) Appl. No.: 16/346,251

(22) PCT Filed: Nov. 1, 2017

(86) PCT No.: PCT/KR2017/012242
§ 371 (c)(1),
(2) Date: Apr. 30, 2019

(87) PCT Pub. No.: WO2018/084562
PCT Pub. Date: May 11, 2018

(65) Prior Publication Data
US 2021/0292759 A1 Sep. 23, 2021

(30) Foreign Application Priority Data
Nov. 1, 2016 (KR) .......................... 10-2016-0144400

(51) Int. Cl.
| C12N 15/115 | (2010.01) |
| A61K 47/61 | (2017.01) |
| A61P 27/02 | (2006.01) |
| A61P 35/00 | (2006.01) |
| A61K 31/713 | (2006.01) |

(52) U.S. Cl.
CPC .......... *C12N 15/115* (2013.01); *A61K 31/713* (2013.01); *A61K 47/61* (2017.08); *A61P 27/02* (2018.01); *A61P 35/00* (2018.01); *C12N 2310/16* (2013.01); *C12N 2310/351* (2013.01)

(58) Field of Classification Search
None
See application file for complete search history.

(56) References Cited

U.S. PATENT DOCUMENTS

| 6,682,886 B1 * | 1/2004 | Gold .................... C12Q 1/6811 435/6.16 |
| 2003/0091640 A1 | 5/2003 | Ramanathan et al. |
| 2015/0094359 A1 * | 4/2015 | Gmeiner ............ A61K 31/7048 514/44 R |

FOREIGN PATENT DOCUMENTS

| KR | 10-2011-0044668 | 4/2011 |
| WO | 2005110489 | 11/2005 |
| WO | 2016-149378 | 9/2016 |

OTHER PUBLICATIONS

Zhao et al. Angew. Chem. Int. 47, 6330-6337 (Year: 2008).*
Wei-Ching Liao et al., "The Application of Stimuli-Responsive VEGF- and ATP-Aptamer-Based Microcapsules for the Controlled Release of an Anticancer Drug, and the Selective Targeted Cytotoxicity toward Cancer Cells", Advanced Functional Materials, vol. 26, pp. 4262-4273, 2016.
Ran Namgung et al., "A Highly Entangled Polymeric Nanoconstruct Assembled by siRNA and its Reduction-Triggered siRNA Release for Gene Silencing", Small, vol. 8, No. 20, pp. 3209-3219, 2012.
Hunho Jo et al., "Aptamer-nanoparticle complexes as powerful diagnostic and therapeutic tools", Experimental & Molecular Medicine, vol. 48, 2016.
Jiehua Zhou et al., "Cell-type-specific, Aptamer-functionalized Agents for Targeted Disease Therapy", Molecular Therapy—Nucleic Acids, vol. 3, e169, 2014.
Jihyun Lee et al., "Self-assembled nanoconstructs modified with amplified aptamers inhibited tumor growth and retinal vascular hyperpermeability via VEGF capturing", Molecular Pharmaceutics, Nol. 14, No. 5, pp. 1460-1468, 2017.
Eric Dausse et al., "Aptamers: a new class of oligonucleotides in the drug discovery pipeline?", Current Opinion in Pharmacology, vol. 9, pp. 602-607, 2009.
Adela R. Cardones et al., "VEGF Inhibitors in Cancer Therapy", Current Pharmaceutical Design, vol. 12, pp. 387-394, 2006.
Naveen S. Vasudev et al., "Anti-angiogenic therapy for cancer: current progress, unresolved questions and future directions", Angiogenesis, vol. 17, pp. 471-494, 2014.

(Continued)

*Primary Examiner* — Brian Whiteman
(74) *Attorney, Agent, or Firm* — Lex IP Meister, PLLC

(57) ABSTRACT

The present invention relates to a method for producing dextran polymer-based amplified nucleic acid aptamer nanoconstructs which efficiently and selectively capture a specific target molecule, the method comprising linking a short nucleic acid sequence or a complementary sequence for formation of nanoconstructs and a nucleic acid aptamer sequence for capture of the specific target molecule to a dextran polymer by a chemical reaction, mixing the resulting polymer/nucleic acid substances with each other to form nanostructures, subjecting the nanostructures to rolling circle amplification, thereby forming a nucleic acid aptamer having a repeated structure. The dextran polymer-based amplified nucleic acid aptamer nanoconstructs have the effect of efficiently and selectively capturing a specific target molecule.

9 Claims, 8 Drawing Sheets

Specification includes a Sequence Listing.

(56) References Cited

OTHER PUBLICATIONS

T Kamba et al., "Mechanisms of adverse effects of anti-VEGF therapy for cancer", British Journal of Cancer, 2007, vol. 96, pp. 1788-1795, 2007.
Belal Al-Husein, M.S. et al., "Antiangiogenic Therapy for Cancer: An Update", Pharmacotherapy, vol. 32, No. 12, 2012.
Evangelos S. Gragoudas et al., "Pegaptanib for Neovascular Age-Related Macular Degeneration", The New England journal of medicine, vol. 351, pp. 2805-2816, 2004.
Ursula Schmidt-Erfurth et al., "Guidelines for the management of neovascular age-related macular degeneration by the European Society of Retina Specialists (EURETINA)", The British journal of ophthalmology, vol. 98, pp. 1144-1167, 2014.
Christopher E. Tucker et al., "Detection and plasma pharmacokinetics of an anti-vascular endothelial growth factor oligonucleotide-aptamer (NX1838) in rhesus monkeys", Journal of Chromatography B, vol. 732 , pp. 203-212, 1999.
KIPO, Notice of Allowance of KR 10-2016-0144400 dated Jun. 20, 2019.

\* cited by examiner

[Fig. 1]
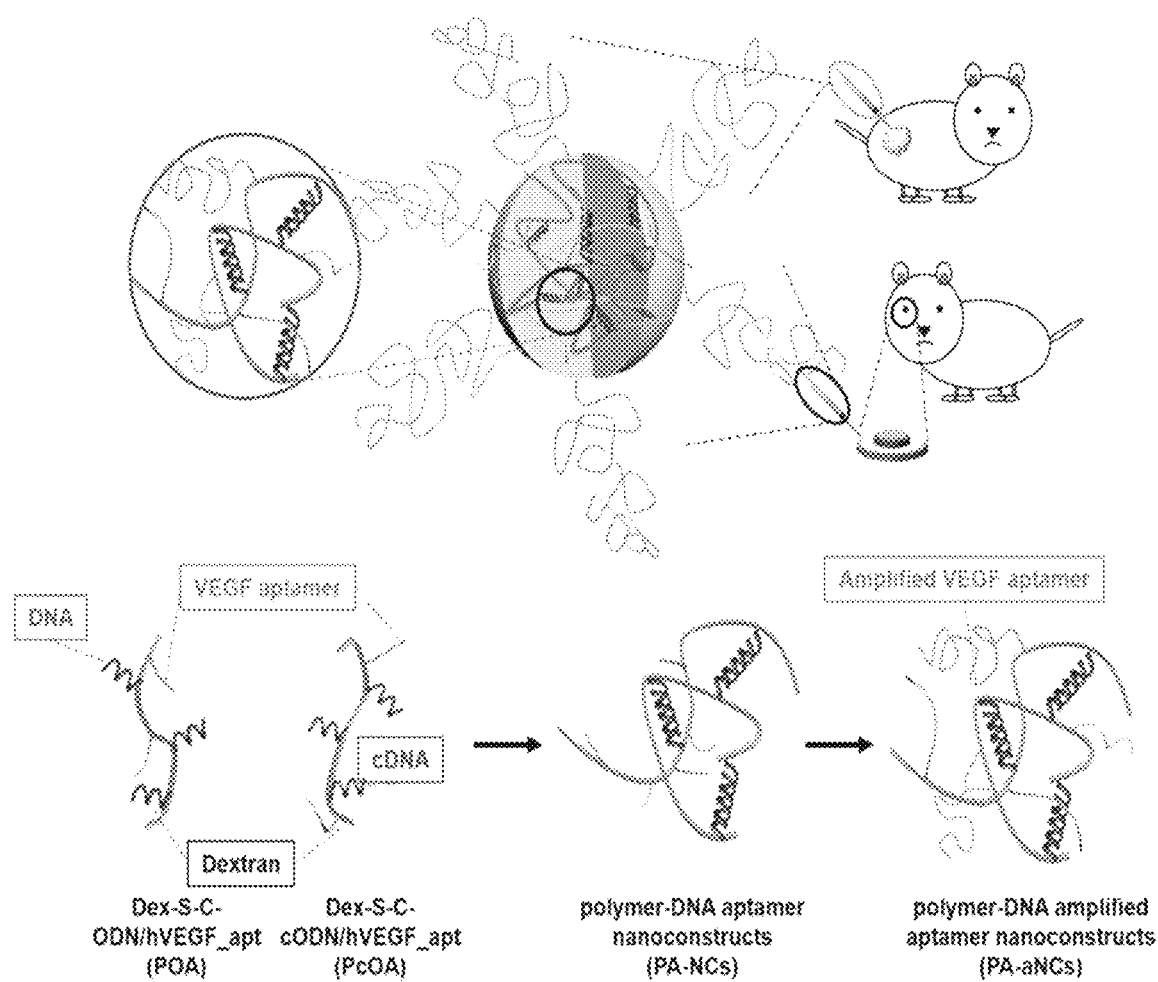

[Fig. 2]
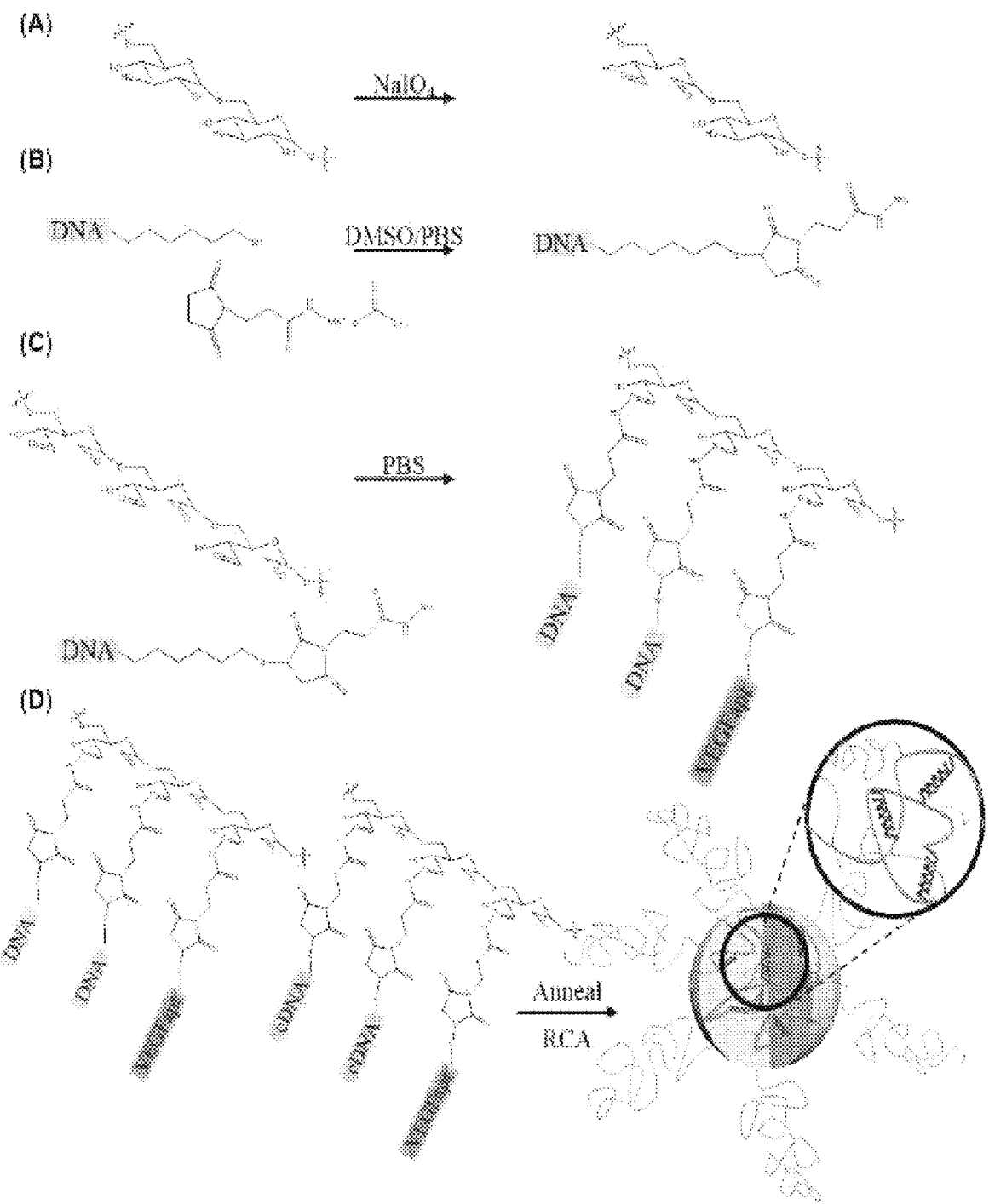

[Fig. 3]
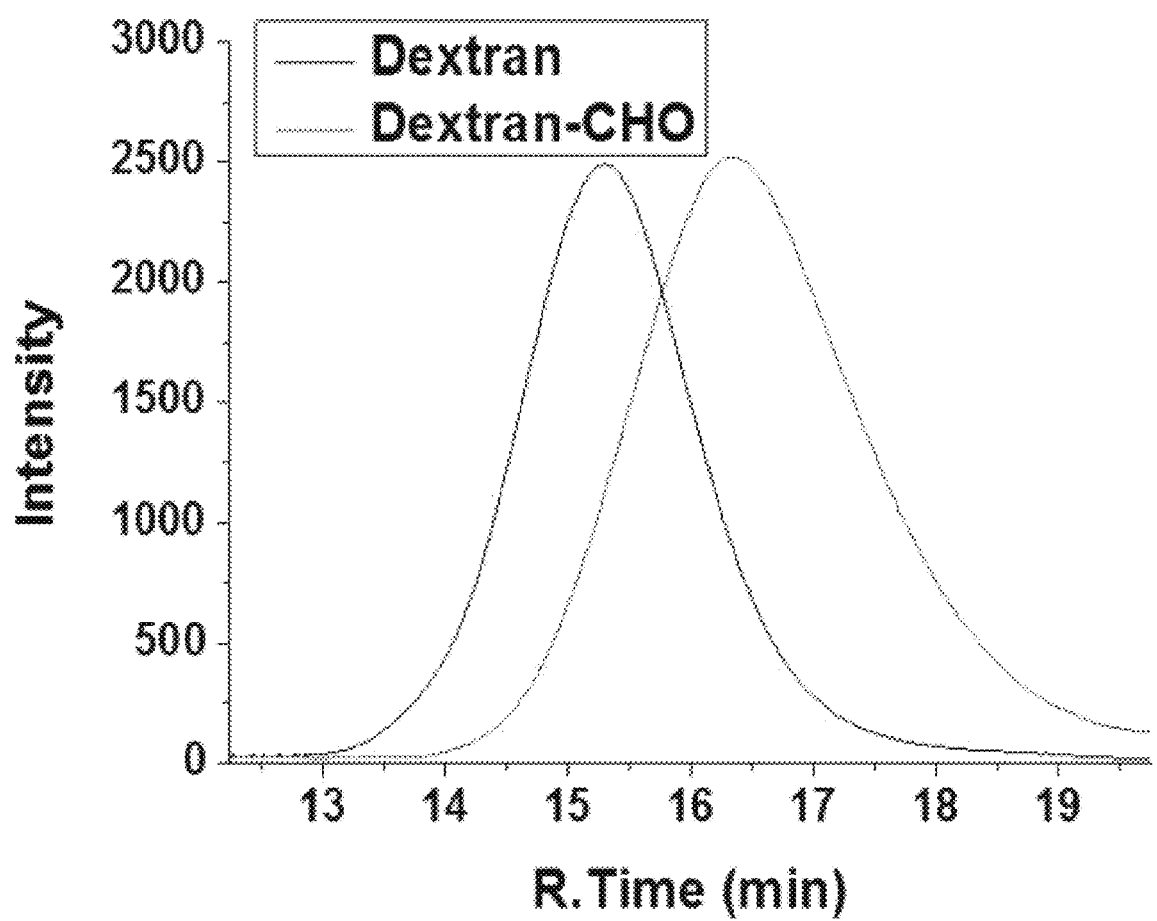

[Fig. 4]
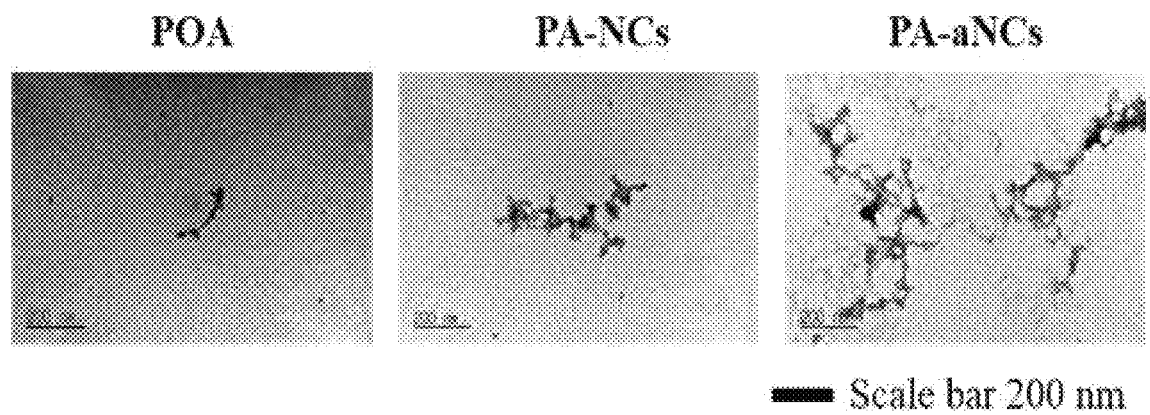
[Fig. 5]
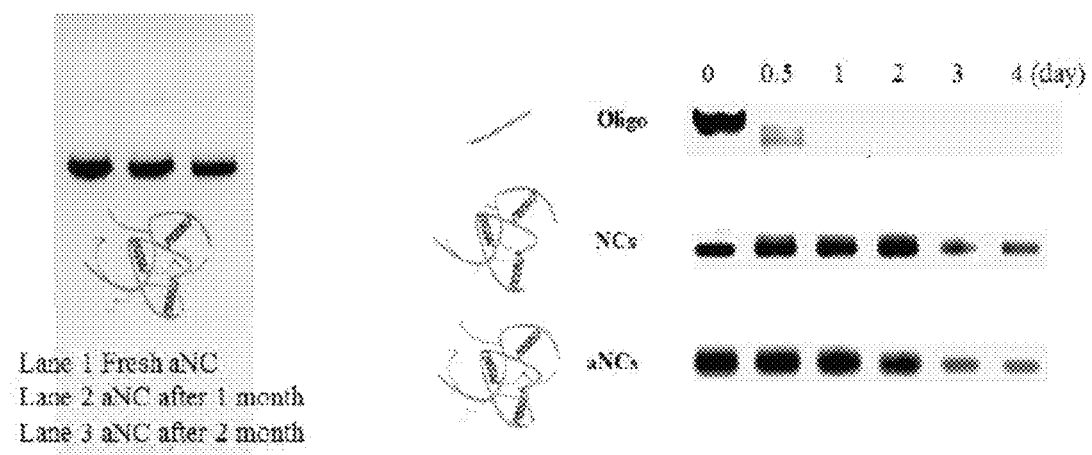

[Fig. 6]
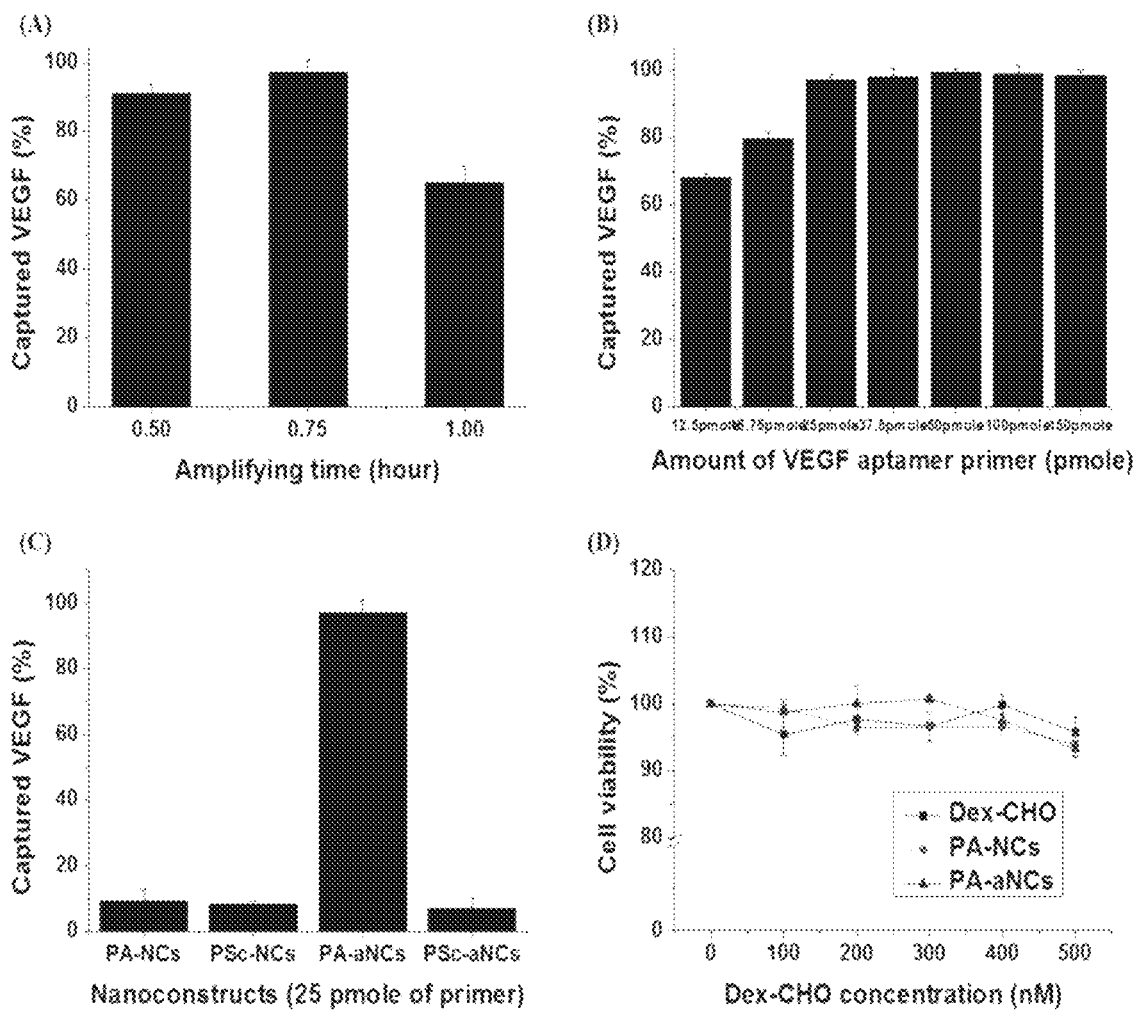

[Fig. 7]
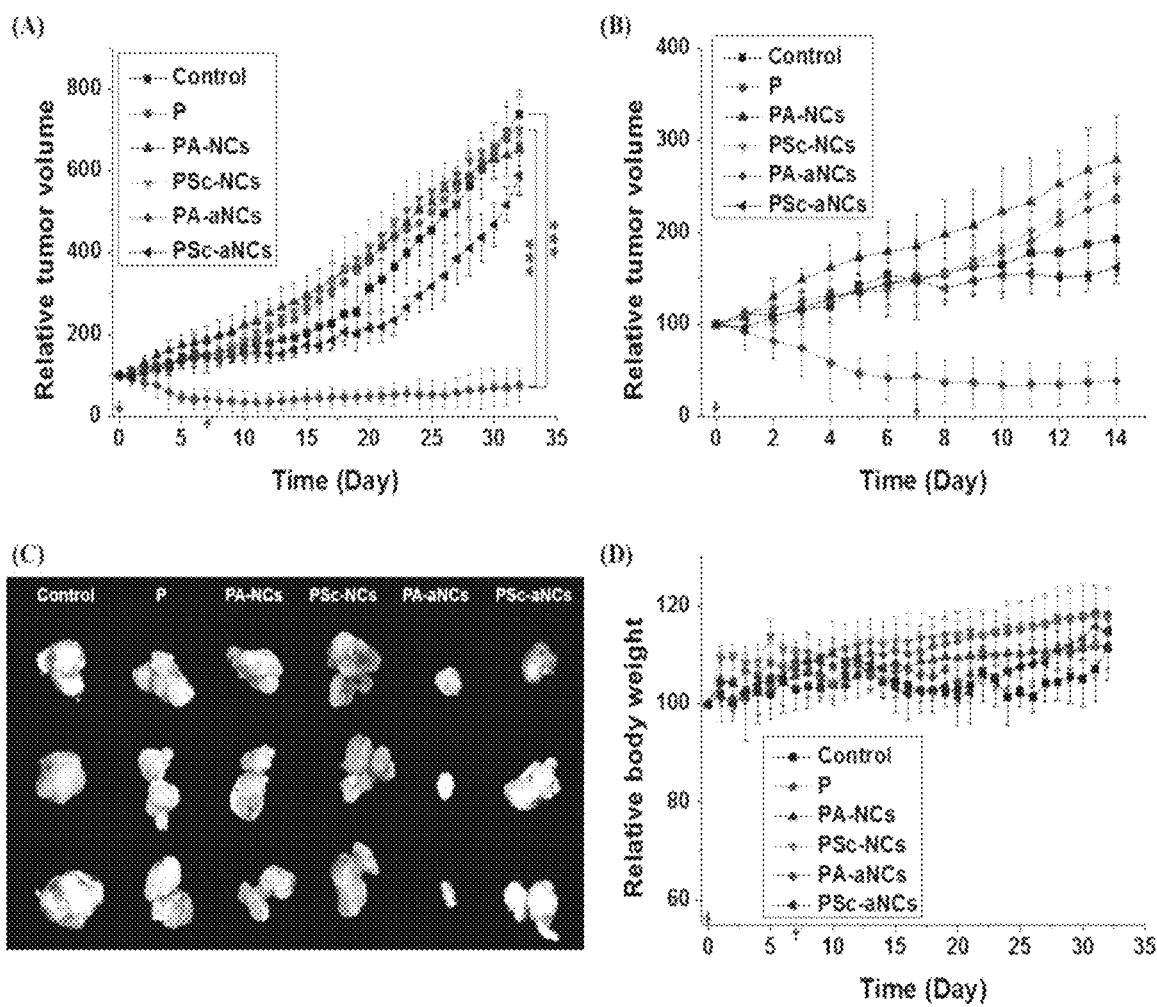

[Fig. 8]
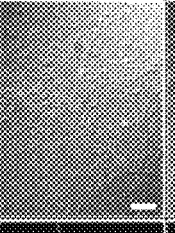

[Fig. 9]
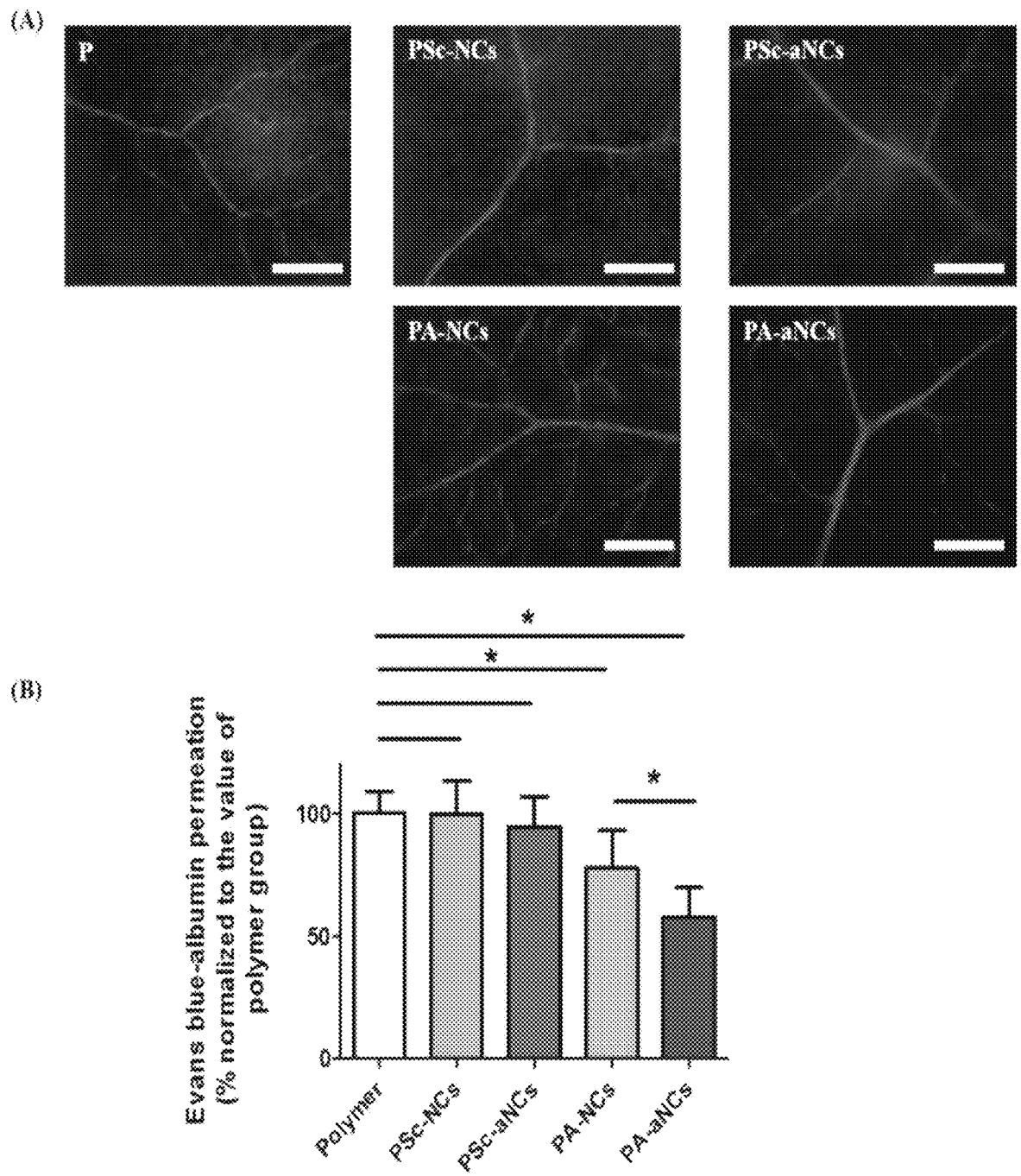

SEQUENCE LISTING

<160> NUMBER OF SEQ ID NOS: 8

<210> SEQ ID NO 1
<211> LENGTH: 25

<212> TYPE: DNA
<213> ORGANISM: Artificial Sequence
<220> FEATURE:
<223> OTHER INFORMATION: [Thiol]ODN

<400> SEQUENCE: 1
ttttccgcaa gatggatcgc acgcc                                            25

<210> SEQ ID NO 2
<211> LENGTH: 25
<212> TYPE: DNA
<213> ORGANISM: Artificial Sequence
<220> FEATURE:
<223> OTHER INFORMATION: [Thiol]cODN

<400> SEQUENCE: 2
ttttggcgtg cgatccatct tgcgg                                            25

<210> SEQ ID NO 3
<211> LENGTH: 30
<212> TYPE: DNA
<213> ORGANISM: Artificial Sequence
<220> FEATURE:
<223> OTHER INFORMATION: [Thiol]VEGF-aptamer

<400> SEQUENCE: 3
ttttcccgtc ttccagacaa gagtgcaggg                                       30

<210> SEQ ID NO 4
<211> LENGTH: 30
<212> TYPE: DNA
<213> ORGANISM: Artificial Sequence
<220> FEATURE:
<223> OTHER INFORMATION: [Thiol]Scramble

<400> SEQUENCE: 4
tttttattat tgaaccgaat tttgtttcat                                       30

<210> SEQ ID NO 5
<211> LENGTH: 12
<212> TYPE: DNA
<213> ORGANISM: Artificial Sequence
<220> FEATURE:
<223> OTHER INFORMATION: [Thiol]DNA-TAMRA

<400> SEQUENCE: 5
ttttgcagta ct                                                          12

<210> SEQ ID NO 6
<211> LENGTH: 66
<212> TYPE: DNA
<213> ORGANISM: Artificial Sequence
<220> FEATURE:
<223> OTHER INFORMATION: [Phos]Circ_cVEGF

<400> SEQUENCE: 6
gatcctaact aaaaaaaaaa ccctgcactc ttgtctggaa gacgggaaaa aaaaaaaaaa      60
ccacac                                                                 66

<210> SEQ ID NO 7
<211> LENGTH: 66
<212> TYPE: DNA
<213> ORGANISM: Artificial Sequence
<220> FEATURE:
<223> OTHER INFORMATION: [Phos]Circ_cSc

```
<400> SEQUENCE: 7
gatcctaact aaaaaaaaaa atgaaacaaa attcggttcc ataataaaaa aaaaaaaaaa        60
ccacac                                                                   66

<210> SEQ ID NO 8
<211> LENGTH: 26
<212> TYPE: DNA
<213> ORGANISM: Artificial Sequence
<220> FEATURE:
<223> OTHER INFORMATION: VEGF-aptamer

<400> SEQUENCE: 8
cccgtcttcc agacaagagt gcaggg                                             26
```

METHOD FOR PRODUCING DEXTRAN POLYMER-BASED, AMPLIFIED NUCLEIC ACID APTAMER NANOCONSTRUCT SELECTIVELY CAPTURING TARGET MOLECULE

TECHNICAL FIELD

The present invention relates to a method for producing dextran polymer-based amplified nucleic acid aptamer nanoconstructs which selectively capture a target molecule, and more particularly to a method for producing dextran polymer-based amplified nucleic acid aptamer nanoconstructs which efficiently and selectively capture a specific target molecule, the method comprising linking a short nucleic acid sequence or a complementary sequence for formation of nanoconstructs and a nucleic acid aptamer sequence for capture of the specific target molecule to a dextran polymer by a chemical reaction, mixing the resulting polymer/nucleic acid substances with each other to form nanostructures, subjecting the nanostructures to rolling circle amplification, thereby forming a nucleic acid aptamer having a repeated structure.

BACKGROUND ART

Recently, aptamers have attracted attention in the treatment and diagnosis of cancer. Aptamers are short (15-40 nucleotides) single-stranded oligonucleotides that form unique three-dimensional structures, have a stem-loop structure, and have the property of binding specifically to certain molecules. Aptamers are compounds that are easily chemically synthesized, chemically easily modified, thermally stable, and have very high specificity for their targets. Aptamer sequences can be obtained using a process called SELEX (selective evolution of ligands by exponential enrichment), and hundreds of aptamer sequences have already been published. Aptamers are often compared with antibodies in that they specifically bind to the target and have no immune response. Aptamers are often compared to antibodies in that they bind specifically to targets, and have no immune response. Many aptamers have been continuously identified, which can bind to various target molecules, including low-molecular compounds, peptides, and membrane proteins. Aptamers are often compared to monoclonal antibodies, because they can bind to target molecules with unique high affinity (usually a pM level) and specificity. In addition, aptamers have high potential as alternative antibodies, since they are often called "chemical antibodies".

The advantages of aptamers are as follows.

Antibodies are difficult to produce due to their large size (~150 kDa) and are also not easy to modify, whereas aptamers have advantages in that they are composed of about 20-60 mer nucleic acids and have a small molecular structure and various necessary modifications thereof are easy. Aptamers are highly stable compared to aptamers. Protein or antibody drugs cannot be stored or transported at room temperature, but aptamers can be stored or transported at room temperature, can maintain their function even after sterilization, and can be regenerated within a short time even after denaturation. Thus, aptamers are very easy to apply for diagnostic applications requiring repeated use for a long time.

A process of screening new aptamers by the SELEX is as follows. First, (i) For DNA and RNA synthesis, a nucleic acid library having various types of nucleic acid molecules is produced using by an in vitro transcription method. (ii) Like antibodies that bind to various kinds of antigens, various nucleic acid structures (or aptamer candidate molecules) in the nucleic acid library have the capability to bind to various target substances and thus a process of screening only nucleic acid structures capable of binding to a target molecule is performed as follows. (iii) Through a method such as affinity chromatography, unbound nucleic acid structures are removed and only nucleic acid structures can be selectively obtained. (iv) Finally, nucleic acid structures are eluted from the target molecule, and the above-described procedures are repeated about 5 to 15 times using the nucleic acid structures obtained by amplifying the nucleic acids, thereby obtaining aptamers showing excellent affinity and specificity.

Initial aptamers obtained by the SELEX as described above may also be subjected to a post-SELEX process to obtain a more stable and potent aptamer. In a representative example, the ribose 2'-OH of an RNA aptamer is substituted with a 2'-F, 2'-$NH_2$, or 2'-O-methyl group. When this modification is performed, an aptamer showing at least 10,000-fold increased stability in blood due to its excellent resistance to nuclease can be obtained. In addition, an aptamer may be conjugated to either a polymer such as polyethylene glycol (PEG), or diacylglycerol or cholesterol, so that the blood half-life of the aptamer can be increased. In addition, an aptamer having biotin conjugated to the 5' or 3' end may be produced, attached to a streptavidin support, and used in the biosensor/chip field (Dausse E. et al., Aptamers: a new class of oligonucleotides in the drug discovery pipeline, *Curr. Opin. Pharmacol*, 2009).

Under this technical background, DNA structures developed using DNA are self-assembled by sequence-specific interactions between complementary nucleic acids, and the nucleotide sequences of the DNA structures which are self-assembled nanoconstructs are controlled so that the structures thereof are changed according to changes in surrounding conditions, such as pH, temperature, and light, thus inducing dynamic motion. Many studies on DNA-conjugated nanoparticles have been conducted. However, when these DNA-conjugated nanoparticles are injected into blood vessels, they can induce toxicity due to their nonspecific accumulation. Accordingly, it is necessary to study drug delivery systems that target only cancer cells.

R. Namgung et al. discloses a method of treating cancer by delivering siRNA using dextran-siRNA nanoconstructs (R. Namgung and W. J. Kim, Small, 2012, 8, No. 20, 3209-3219).

Meanwhile, vascular endothelial growth factor-A (VEGF-A) was first identified as the primary survival factor of vascular endothelial cells. In terms of biological function, VEGF is one of the most potent angiogenic factors and is an important regulator of vascular permeability. VEGF is widely accepted as a major regulator of pathological angiogenesis-related diseases, such as wet-type age-related macular degeneration (AMD), and angiogenic tumor growth. In addition, it is a potent enhancer of vascular permeability, and is also deeply involved in pathogenic vascular leakage-related diseases, including diabetic macular edema.

Anti-VEGF treatment is considered to be the most important treatment for wet AMD, diabetic macular edema and cancer. Various technologies are known, which block the VEGF pathway using (1) antibodies (bevacizumab, and ranibizumab); (2) an aptamer (pegaptanib) for neutralizing VEGF or VEGF receptor (VEGFR); (3) siRNA targeting VEGF mRNA; (4) small-molecular kinase inhibitors (lapatinib, and sunitinib) for VEGF receptor; or (5) soluble VEGF receptor (sVEGFR) that inhibits VEGF/VEGFR interaction (Cardones, A. R. et al., *Current pharmaceutical design* 2006, 12, 387-394; Vasudev, N. S. et al., Angiogenesis 2014, 17, 471-494).

In recent years, examples of the use of many anti-VEGF drugs for the treatment of VEGF-related diseases have been reported. However, these drugs have a problem in that their in vivo efficacy, toxicity and stability under physiological conditions are uncertain (Kamba, T. et al., *British Journal of Cancer* 2007, 96, 1788-1795; Al-Husein, B. et al., *Pharmacotherapy: The Journal of Human Pharmacology and Drug Therapy* 2012, 32, 1095-1111).

Pegaptanib, an RNA aptamer for VEGF165, was first approved by the FDA as an anti-VEGF drug for the treatment of angiogenic AMD. This aptamer drug is safe, but is not so efficient compared to other alternative anti-VEGF drugs, such as anti-VEGF monoclonal antibody ranibizumab, and aflibercept comprising VEGF receptor 1 and 2 fused to the Fc domain of IgG, and hence is rarely used in clinical practice (Gragoudas, E. S. et al., *The New England journal of medicine* 2004, 351, 2805-2816; Schmidt-Erfurth, U. et al., *The British journal of ophthalmology* 2014, 98, 1144-1167). The binding affinity of the anti-VEGF aptamer for VEGF and the in vivo stability thereof are major factors that determine the biological effect of the anti-VEGF aptamer. Pegaptanib has a problem in that it has a relatively short in vivo half-life (9.3 hours after intravenous injection, and 12 hours after subcutaneous injection), even when it is structurally modified to increase its resistance to nuclease (Tucker, C. E. et al., *Journal of chromatography. B, Biomedical sciences and applications* 1999, 732, 203-212).

Accordingly, the present inventors have found that when a short nucleic acid sequence or a complementary sequence for formation of nanoconstructs and a nucleic acid aptamer sequence for capture of a specific target molecule are linked to a dextran polymer by a chemical reaction, the resulting polymer/nucleic acid substances are mixed with each other to form nanostructures, and the nanostructures are subjected to rolling circle amplification, thereby forming a nucleic acid aptamer, it may have high target molecule capture efficiency, and the use of this aptamer nanoconstruct is effective in treating cancer and macular edema diseases by selectively capturing vascular endothelial cell growth factor which is a disease-causing substance, thereby completing the present invention.

DISCLOSURE OF INVENTION

Technical Problem

It is an object of the present invention to provide a method for producing dextran polymer-based amplified nucleic acid aptamer nanoconstructs which efficiently and selectively capture a specific target molecule.

Another object of the present invention is to provide a composition for prevention or treatment of cancer and macular edema, which contains dextran polymer-based amplified nucleic acid aptamer nanoconstructs as active ingredients.

Technical Solution

To achieve the above objects, the present invention provides a method for producing dextran polymer-based amplified nucleic acid aptamer nanoconstructs which selectively capture a target molecule, the method comprising the steps of: (a) linking each of an aptamer sequence (Apt) for the target molecule and a DNA sequence capable of forming nanoconstructs to a dextran polymer, thereby producing a dextran polymer-based DNA aptamer (Dex-DNA-Apt); (b) linking each of an aptamer sequence (Apt) for the target molecule and a sequence (cDNA) complementary to the DNA sequence to the dextran polymer, thereby producing a dextran polymer-based cDNA aptamer (Dex-cDNA-Apt) having a dextran polymer-based cDNA sequence; (c) mixing the Dex-DNA-Apt produced in step (a) with the Dex-cDNA-Apt produced in step (b), followed by annealing, thereby producing nanoconstructs (NCs); and (d) subjecting the nanoconstructs to rolling circle amplification to amplify the aptamer (Apt), thereby producing nanoconstructs (aNCs) having an amplified aptamer Apt for the target molecule.

The present invention also provides dextran polymer-based amplified nucleic acid aptamer nanoconstructs, produced by the production method.

The present invention also provides a composition for prevention or treatment of cancer and macular edema, which contains dextran polymer-based amplified VEGF-targeting nucleic acid aptamer nanoconstructs as active ingredients.

BRIEF DESCRIPTION OF THE DRAWINGS

FIG. 1 schematically illustrates a method of producing dextran polymer-based amplified nucleic acid aptamer nanoconstructs that selectively capture a target molecule according to an example of the present invention.

FIG. 2 schematically illustrates a reaction that produces dextran polymer-based amplified nucleic acid aptamer nanoconstructs that selectively capture a target molecule according to an example of the present invention.

FIG. 3 is a graph confirming the synthesis of Dextran-CHO according to an example of the present invention.

FIG. 4 depicts TEM images showing the sizes of Dex-DNA/VEGF, NCs and aNCs according to an example of the present invention.

FIG. 5 shows the results of enzyme-linked immunosorbent assay performed to analyze the stability of aNCs according to an example of the present invention.

FIG. 6A shows the result of evaluation on VEGF capture ability.

FIG. 6B shows the result of evaluation on the amount of the primer (oligomer aptamer) in PA-aNCs for VEGF capture.

FIG. 6C demonstrates the result that VEGF-amplified VEGF aptamer contributes to efficient VEGF capture ability.

FIG. 6D shows the result of an in vivo toxicity test for samples (P (polymer), PA-NCs (polymer-DNA aptamer nanoconstructs) and PA-aNCs (polymer-DNA amplified aptamer nanoconstructs)).

FIG. 7A shows the result of tumor regression effects for P, PA-NCs, PSC-NCs, PA-aNCs and PSc-aNCs.

FIG. 7B shows the result of stability for PA-aNCsin serum.

FIG. 7C shows the result of tumor regression effects for the tumor tissue.

FIG. 7D shows the result of evaluation on toxicity for PA-aNC.

FIG. 8 depicts images showing the results of histological examination performed to evaluate the effect of aNCs on VEGF capture and cancer growth inhibition in rat cancer models according to an example of the present invention.

FIG. 9A shows images that aNCs_VEGF aptamer effectively captured VEGF.

FIG. 9B shows evans blue dye permeation result for evaluating the effect of aNCs on VEGF capture and cancer growth inhibition in rat macular edema models.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

In the present invention, dextran polymer-based amplified nucleic acid aptamer nanoconstructs which efficiently and selectively capture a specific target molecule were produced. First, a short nucleic acid sequence or a complementary sequence for formation of nanoconstructs and a nucleic acid aptamer sequence for capture of a specific target molecule were linked to a dextran polymer by a chemical reaction, the resulting polymer/nucleic acid substances were mixed with each other to form nanostructures, and the nanostructures were subjected to rolling circle amplification so as to have high target molecule capture efficiency, thereby forming a nucleic acid aptamer having a repeated structure.

In the present invention, with reference to the platform of R. Namgung et al. (Namgung and W. J. Kim, Small, 2012, 8, No. 20, 3209-3219), that is, based on the disclosure that nanoconstructs are produced by linking siRNA to dextran, nanoconstructs were produced by linking DNA to dextran. In addition, a VEGF-targeting aptamer was linked to dextran and amplified, thereby increasing the targetability thereto to VEGF.

Therefore, in one aspect, the present invention is directed to a method for producing dextran polymer-based amplified nucleic acid aptamer nanoconstructs which selectively capture a target molecule, the method comprising the steps of: (a) linking each of an aptamer sequence (Apt) for the target molecule and a DNA sequence capable of forming nanoconstructs to a dextran polymer, thereby producing a dextran polymer-based DNA aptamer (Dex-DNA-Apt); (b) linking each of an aptamer sequence (Apt) for the target molecule and a sequence (cDNA) complementary to the DNA sequence to the dextran polymer, thereby producing a dextran polymer-based cDNA aptamer (Dex-cDNA-Apt) having a dextran polymer-based cDNA sequence; (c) mixing the Dex-DNA-Apt produced in step (a) with the Dex-cDNA-Apt produced in step (b), followed by annealing, thereby producing nanoconstructs (NCs); and (d) subjecting the nanoconstructs to rolling circle amplification to amplify the aptamer (Apt), thereby producing nanoconstructs (aNCs) having an amplified aptamer Apt for the target molecule.

In another aspect, the present invention is directed to dextran polymer-based amplified nucleic acid aptamer nanoconstructs, produced by the above-described production method.

FIG. 1 schematically illustrates a method of producing dextran polymer-based amplified nucleic acid aptamer nanoconstructs that selectively capture a target molecule according to an example of the present invention. In particular, it shows the case in which the target molecule is vascular endothelial growth factor (VEGF).

In the present invention, the target molecule may be selected from the group consisting of vascular endothelial growth factor (VEGF), bovine serum albumin (BSA), adenosine triphosphate (ATP), hepatitis C virus (HCV) and HIV-1. As the target molecule, any target substance for which a DNA-based aptamer has been developed may be used. In other words, any substances other than VEGF may be selectively captured as long as the aptamer design is satisfied. For example, an aptamer for BSA may be selected and used to produce dextran-based nanoconstructs that may selectively capture BSA.

In the present invention, VEGF, which is often found around cancer and is a substance that causes macular edema, may be selected as a specific target protein in the production of the dextran polymer-based amplified nucleic acid aptamer nanoconstructs that selectively and efficiently capture the specific target molecule. Thus, VEGF may preferably be selected and used, but is not limited thereto.

In the present invention, the DNA sequence capable of forming nanoconstructs may be any sequence that enables base parting (a/t, or g/c). In other words, it may be a complementary sequence which may be random. Preferably, the DNA sequence capable of forming nanoconstructs may be TTT TCC GCA AGA TGG ATC GCA CGC C (ODN, 25 nts, SEQ ID NO: 1) and TTT TGG CGT GCG ATC CAT CTT GCG G (cODN, 25 nts, SEQ ID NO: 2). TTTT in 5'-TTTT is an elongation for increasing chemical reactivity with dextran.

In one embodiment of the present invention, when the target molecule is VEGF, the aptamer sequence (Apt) for VEGF may be CCCGTCTTCCAGACAAGAGT-GCAGGG-3' (SEQ ID NO: 8), which is a VEGF-targeting aptamer sequence having a length of 26 nucleotides (from C to G). TTTT might be added to 5'-position, and TTTT in 5'-TTTT is an elongation for increasing chemical reactivity with dextran.

In a preferred embodiment of the present invention, for selective interaction with VEGF, a VEGF-targeting aptamer sequence (VEGFapt) is chemically linked to the dextran polymer. In addition, for formation of the nanoconstructs, a short nucleic acid sequence (DNA) is also chemically linked to dextran. The dextran polymer-based nucleic acid aptamer (Dex-DNA/VEGF) formed as described above and the Dex-cDNA/VEGF produced using the complementary sequence are mixed with each other and subjected to an annealing process (in which temperature is elevated and lowered), thereby forming nanoconstructs (NCs). The above-described procedures are performed using a method known in the art (R. Namgung and W. J. Kim, Small, 2012, 8, No. 20, 3209-3219). Next, rolling circle amplification (RCA) is performed to amplify the VEGFapt of the NCs, thereby forming aNCs.

The size of the dextran polymer-based DNA aptamer may vary depending on the molecular weight of dextran or the conjugated proportion of DNA. It may be preferably 100 to 400 nm, more preferably 200 to 300 nm.

In the present invention, the size of the nanoconstructs (NCs) produced through the annealing process may vary depending on the molecular weight of dextran or the conjugated proportion of DNA. It may be preferably 200 to 600 nm, more preferably 400 to 450 nm. Further, the size of the amplified nanoconstructs (aNCs) produced by amplifying NCs may vary depending on the molecular weight of dextran or the conjugated proportion of DNA, the number of aptamers, and the amplification time of aptamer. It may be preferably 400 to 1,000 nm, more preferably 600 to 650 nm.

In an embodiment of the present invention, it could be found that the use of the dextran polymer-based amplified nucleic acid aptamer nanoconstructs is effective in treating cancer and macular edema diseases by selectively capturing vascular endothelial cell growth factor (VEGF) which is a disease-causing substance, Therefore, in still another aspect, the present invention is directed to a composition for prevention or treatment of cancer and macular edema, which contains dextran polymer-based amplified VEGF-targeting nucleic acid aptamer nanoconstructs as active ingredients.

In yet another aspect, the present invention is directed to a method for prevention or treatment of cancer or macular edema, the method comprising administering a composition which contains dextran polymer-based amplified VEGF-targeting nucleic acid aptamer nanoconstructs as active ingredients.

In a further aspect, the present invention is directed to the use of a composition for prevention or treatment of cancer or macular edema, which contains dextran polymer-based amplified VEGF-targeting nucleic acid aptamer nanoconstructs as active ingredients.

In the present invention, the prevention or treatment of cancer or macular edema may be performed by allowing the aptamer to bind to vascular endothelial growth factor.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Production of Dextran Polymer-Based Amplified Nucleic Acid Aptamer Nanoconstructs (aNCs)

For selective interaction with VEGF, a VEGF-targeting aptamer sequence (VEGFapt; SEQ ID NO: 3) was chemically linked to a dextran polymer. In addition, for formation of nanoconstructs, a short nucleic acid sequence (DNA) was also chemically linked to dextran. The dextran polymer-based nucleic acid aptamer (Dex-DNA/VEGF) formed as described and the Dex-cDNA/VEGF formed using a complementary sequence were mixed with each other and subjected to an annealing process (in which temperature was elevated and lowered), thereby forming nanoconstructs (NCs). The above-described procedures were performed using a method known in the art (R. Namgung and W. J. Kim, Small, 2012, 8, No. 20, 3209-3219). Aldehyde-functionalized dextran was synthesized (FIG. 2(A)), and a hydrazine-modified DNA (DNA-S-C-hydrazide) was synthesized by sulfide-carbon linkage (FIG. 2(B)), and Dex-CHO and DNA-S-C-hydrazide were conjugated to each other (FIG. 2(C)). To amplify the VEGFapt of the obtained NCs, rolling circle amplification (RCA) was performed, thereby forming aNCs (FIG. 2(D)).

A detailed process for producing the dextran polymer-based amplified nucleic acid aptamer nanostructures (aNCs) is as follows.

Synthesis of Aldehyde-Functionalized Dextran (Dex-CHO)

Dextran (500 mg, glucose unit: 3.08 mmol) was dissolved in 10 mL of deionized water. Sodium periodate (660 mg, 3.08 mmol) was dissolved in 20 mL of deionized water. The prepared sodium periodate solution was added dropwise to the dextran solution, and the mixture was vigorously stirred at 4° C. for 12 hours. The produced solution was dialyzed with deionized water through a 3.5 kDa dialysis membrane in a dark place at 4° C. for 2 days, and then freeze-dried, thereby obtaining 477 mg of white powder (yield: 95.4%) (FIG. 2(A)).

The aldehyde content of Dex-CHO was measured according to a conventional method (Namgung, R et al., Small 2012, 8, 3209-3219). Dex-CHO (10 mg) was dissolved in hydroxylamine hydrochloride solution (5 mL, 0.25 M) having a pH of 2.10. The mixture was sonicated for 1 hour, and stored in a dark room at room temperature for 12 hours. The degree of periodate decomposition was measured by titration of the HCl produced in the reaction of aldehyde with the measured amount of hydroxylamine hydrochloride. It was titrated with standard NaOH (0.1N) solution until it reached a pH of 2.10. The aldehyde content of the sample was calculated by comparing the titers of NaOH obtained from a standard curve by plotting the volume of NaOH relative to the amount of 2,4-dihydroxybenzaldehyde. The average cleavage degree was calculated as 84.6%.

Oxidative ring cleavage of dextran was performed by gel permeation chromatography (Shimadzu, Kyoto, Japan) 803HQ, ShowaDenko, Tokyo, Japan) with a refractive index detector (RID-10A, Shimadzu, Kyoto, Japan) using a column (SB-806M). Deionized water was used as an eluent at a flow rate of 1 mL/min, and the column temperature was maintained at 40° C. The molecular weight of Dex-CHO slightly decreased compared to that of the original dextran.

Synthesis of Hydrazine-Modified DNA (DNA-S-C-Hydrazide) by Sulfide-Carbon Linkage In order to make a free thiol group at the 5'-end of single-stranded DNA, 2 equivalents of TCEP-HCl was added to 1 equivalent of 5'-thiol-blocked DNA in PBS buffer (pH 8.0), and vigorously stirred at room temperature for 30 minutes. After deprotection, the reaction product was purified by centrifugal filtration (Amicon Ultra-4, MWCO 3 kDa). DNA (1 equivalent) and BMPH (10 equivalents) were allowed to react in DMSO/PBS buffer (pH 8.0) at room temperature for 12 hours, thereby synthesizing DNA-S-C-hydrazide. After the reaction, an excess of BMPH was removed by centrifugal filtration (Amicon Ultra-4, MWCO 3 kDa), and the produced solution was freeze-dried, thereby obtaining DNA-S-C-hydrazide. This process was also performed on [Thiol]ODN (SEQ ID NO: 1), [Thiol]cODN (SEQ ID NO: 2), [Thiol]VEGF_aptamer (SEQ ID NO: 3), [Thiol]Scramble (SEQ ID NO: 4), and [Thiol]DNA-TAMRA (SEQ ID NO: 5).

Conjugation of Dex-CHO with DNA-S-C-Hydrazide

Dex-SCO (1 equivalent), ODN-SC-hydrazide (5 equivalents) and VEGF_aptamer-SC-hydrazide (2.5 equivalents) were allowed to react in PBS buffer for 24 hours with stirring, thereby producing a Dex-SC-ODN/VEGF_aptamer (POA) conjugate. After the reaction, Amicon Ultra-4 (MWCO 10 kDa) was centrifuged at 3000 g for 10 minutes, and then freeze-dried. Dex-S-C-cODN/VEGF_aptamer (PcOA), Dex-S-C-ODN/Sc (POSc) and Dex-S-C-cODN/Sc (PcOSc) conjugates were produced according to the same process (FIG. 2(C)).

Production of Circularized DNA Template

According to the CircLigase™ protocol, circularized DNA was produced. Phosphorylate modified DNA was mixed with ATP, MgCl$_2$ and ligase in buffer. After mixing, the solution was incubated at 60° C. for 12 hours. After the enzyme deactivation process, the produced solution was treated with 20 U of exonuclease I and 100 U of exonuclease III at 37° C. for 30 minutes. Then, the enzyme deactivation process was also performed. The circularized DNA was checked by denatured polyacrylamide electrophoresis. After purification of DNA PrepMate™-II, gel electrophoresis was performed, and the concentration was measured by UV absorption at 280 nm. The circularized DNA templates used were [Phos Circ_cVEGF (SEQ ID NO: 6) and Phos Circ_cSc (SEQ ID NO: 7).

Production of Polymer-Amplified Aptamer Nanoconstructs (PA-aNCs) PA-NCs were produced by hybridization of both POA and PcOA using an annealing process. After performing a rolling circle amplification (RCA) process for the production of PA-aNCs, the Φ29 polymerase protocol was performed. The prepared circularized Circ_cVEGF and PA-NC were added to a buffer containing dNTP, BSA and Φ29 polymerase. After mixing, the solution was incubated at 30° C. for a predetermined time. The produced solution was incubated at 80° C. for enzyme deactivation, and then cooled slowly. PSc-NCs and PSc-aNCs were also produced by the same process (FIG. 2(D)).

The sequences of the DNA and oligodeoxynucleotides (ODNs) used in the Examples are shown in Table 1 below. Modifications of the 5' end are shown in brackets. [SH] indicates modification with thiol, and [Phos] indicates modification with phosphorylate.

Example 2: Examination of VEGF Capture Property of aNCs

In order to evaluate the capture effect of the prepared aNCs in VEGF-containing solution, aNCs were added to distilled water containing 500 pg/ml of VEGF, and VEGF capture was performed at 36° C. for 10 hours. After the capture was performed, captured VEGF and non-captured VEGF were separated from each other using a PD-10 column. Then, the amount of VEGF captured was analyzed by enzyme-linked immunosorbent assay (ELISA).

First, the change in percent capture of VEGF with the amplification time of the nucleic acid aptamer was examined, and based on the results, an amplification time of 45 minutes was used as a reference. In addition, it was examined how much the nucleic acid aptamer primer interacts with VEGF depending on the amount of the nucleic acid plumper primer, and as a result, it could be seen that 25 pmole of primer effectively reacted with 500 pg/ml of VEGF. Through this method, the VEGF capture rate each of

TABLE 1

| Name | Sequence (5'-3') | SEQ ID No: | Length (bps) |
|---|---|---|---|
| [Thiol]ODN | [SH]-TTT TCC GCA AGA TGG ATC GCA CGC C | 1 | 25 |
| [Thiol]cODN | [SH]-TTT TGG CGT GCG ATC CAT CTT GCG G | 2 | 25 |
| [Thiol]VEGF_aptamer | [SH]-TTT TCC CGT CTT CCA GAC AAG AGT GCA GGG | 3 | 30 |
| [Thiol]Scramble | [SH]-TTT TTA TTA TTG AAC CGA ATT TTG TTT CAT | 4 | 30 |
| [Thiol]DNA-TAMRA | [SH]-TTT TGC AGT ACT-[TAMRA] | 5 | 12 |
| [Phos]Circ_cVEGF | [PHOS]-GAT CCT AAC TAA AAA AAA AAC CCT GCA CTC TTG TCT GGA AGA CGG GAA AAA AAA AAA CCA CAC | 6 | 66 |
| [Phos]Circ_cSc | [PHOS]-GAT CCT AAC TAA AAA AAA AAA TGA AAC AAA ATT CGG TTC CAT AAT AAA AAA AAA AAA CCA CAC | 7 | 66 |

(1) Confirmation of Synthesis of Dextran-CHO

It was confirmed by GPC that the peak of Dextran-CHO appeared at a later time than that of dextran (FIG. 3).

(2) Measurement of Size of aNCs

The size of aNCs was measured by TEM and DLS. sNCs had a size of about 600 nm, NCs had a size of about 400 nm, and the VEGF aptamer had a size of about 200 to 300 nm. The results are shown in Table 2 below and FIG. 4.

TABLE 4

| DLS measurement | Size (nm) |
|---|---|
| Dex-DNA/VEGF | 285 ± 15 |
| NCs | 420 ± 10 |
| aNCs | 620 ± 30 |

(3) Evaluation of Stability of aNCs

The stability of aNCs was evaluated at room temperature for 2 months or under FBS conditions for 5 days. As a result, it could be confirmed that aNCs were stable at room temperature for 2 months and maintained under FBS conditions for 4 days (FIG. 5).

NCs_V, NCs_Sc, NCs_aV and NCs_aSc was calculated (primer: 25 pmole; amplified for 45 minutes) (FIG. 6).

As shown in FIG. 6(A), when amplification was performed for 0.75 hours, PA-aNCs (polymer-DNA amplified aptamer nanoconstructs) showed the most efficient VEGF capture ability. In addition, the amount of the primer (oligomer aptamer) in PA-aNCs for efficient VEGF capture was optimized by a similar process, and 25 pmole of the primer in PA-aNCs showed an efficient VEGF capture property at a given VEGF concentration (FIG. 6(B)). Accordingly, amplification was performed for 0.75 hours, and VEGF capture analysis was additionally performed using PA-aNCs having 25 pmole of the primer per 50 pg [VEGF]. Finally, a VEGF-containing solution was mixed with each of PA-NCs (polymer-DNA aptamer nanoconstructs), PSc-NCs (polymer-sulfide-carbon nanoconstructs), PA-aNCs (polymer-DNA amplified aptamer nanoconstructs) and PSc-aNCs (polymer-sulfide-carbon amplified aptamer nanoconstructs) ([primer]=25 pmole), and stirred at 37° C. for 12 hours (FIG. 6(C)). After purification of free-VEGF with a PD-10 column, the amount of unbound VEGF was analyzed using a VEGF ELISA kit. About 97.0% of VEGF was captured by PAc-aNCs compared to lower VEGF capturing efficiencies for PA-NCs (9.21%), PSc-NCs (8.18%), and PSc-aNCs (7.12%). These results imply that the VEGF-amplified VEGF aptamer contributes to efficient VEGF capture ability.

VEGF is overexpressed in solid tumor tissue, and binds to VEGF receptor (VEGFR) tyrosine kinase to activate various signaling pathways, including angiogenesis and tumorigenesis. Thus, tumor growth can be inhibited by anti-VEGF treatment, such as removing VEGF by an anti-VEGF agent. In this regard, it can be seen that PA-aNCs can more efficiently inhibit tumor growth than PA-NCs having a short oligomer aptamer.

To examine the non-specific cytotoxicity of each sample, PA-aNCs were prepared and subjected to an in vivo toxicity test (FIG. 6(D)). All the samples (P (polymer), PA-NCs (polymer-DNA aptamer nanoconstructs) and PA-aNCs (polymer-DNA amplified aptamer nanoconstructs)) showed no significant toxicity in A549 cells, suggesting that these samples may be applied for in vivo tumor regression tests in VEGF-induced retinal vascular hyperpermeability models and for treatment.

Example 3: Evaluation of the VEGF Capture and Cancer Growth Inhibitory Effects of aNCs in Mouse Cancer Models VEGF in mouse cancer models was captured using aNCs, and the inhibition of cancer growth by the capture was evaluated. As the mice, Balb/c nu/nu female mice were used. A549 cancer cells were injected into mice ($1 \times 10^8$ cells/mouse), and the aNCs_VEGF aptamer or aNCs_Sc was injected into the mice when the tumor reached a size of about 80 mm$^3$. After 7 days, second injection was performed. The size of the cancer and the body weight of the mice were monitored continuously for 33 days, and as a result, it could be confirmed that when the aNCs_VEGF aptamer was injected twice, the growth of the cancer was significantly inhibited compared to other cases. The body weight of the mice did not significantly change during the monitoring period (FIG. 7).

As shown in FIG. 7(A), P, PA-NCs, PSC-NCs, PA-aNCs and PSc-aNCs were injected into tumors (mean size on day 0: 66 mm$^3$) (day 0 and day 7). The groups treated with each of P, PA-NCs, PSc-NCs and PSc-aNCs exhibited moderate tumor regression effects (P: 6.6-fold increase; PA-NCs: 6.5-fold increase; PSc-NCs: 7.0-fold increase; and Psc-aNCs: 5.9-fold increase), which were sufficient for efficient anti-tumor treatment. On the contrary, the mice treated with PA-aNCs showed a 0.74-fold decrease in the tumor size on 32 days. Since the tumor growth inhibitory efficiency of PA-NCs is 8.8-fold lower than that of PA-aNCs, amplification of the abdominal sequence is considered to be a crucial factor for the capture of the target molecule.

In the present invention, it is assumed that the aptamer of PA-NCs does not substantially interact with the target molecule, since it is not exposed to the surface of the nanoconstructs.

As shown in FIG. 7(B), after injection of PA-aNCs (day 0 and day 7), tumor growth was inhibited up to day 5, suggesting that PA-aNCs were stable in serum. This result is because the inhibition of the VEGF pathway in the tumor tissue due to initial VEGF capture of PA-aNCs significantly contributed to the inhibition of tumor growth. As shown in the body weight profile, there was no significant decrease in body weight on day 32, indicating that PA-aNC is non-toxic (FIG. 7(D)).

In addition, for histological examination, on 4 days after first sample injection, the mice were sacrificed and cancer tissue was collected therefrom and subjected to H & E staining and CD31 staining. In the case of the mouse cancer injected with the aNCs_VEGF aptamer, it could be confirmed that blood vessels were less expressed than those in other cases, and inflammation and the apoptosis of the cancer cells could be seen (FIG. 8).

Tumor tissue stained with CD31 after treatment or non-treatment with P, PA-NCs, PSc-NCs or PSc-aNCs showed high FITC fluorescence, whereas fluorescence was hardly observed in the PA-aNC group. The above-described results indicate that VEGF capture by PA-aNCs inhibits tumor growth by inhibiting angiogenesis in tumor areas.

Example 4: Evaluation of the VEGF Capture and Macular Edema-Preventing/Treating Effects of aNCs in Macular Edema Models VEGF in macular edema models was captured using aNCs, and the prevention and treatment of macular edema by the capture were evaluated.

Each of Dextran-CHO, the NCs_VEGF aptamer, the NCs_Sc, the aNCs_VEGF aptamer, and aNCs_Sc was mixed with 60 ng of VEFG and injected to the eyes of mice. After one day, Evans blue dye was injected into the heart, and after 2 hours, the mice were sacrificed and the eyeballs were extracted. After the retina was peeled off, and fluorescent images of the extracted eyeballs were obtained using a fluorescence microscope. In the case of the sample that failed to capture VEGF (test group), it could be seen that the blood vessels were loosened and the Evans blue dye was out of the blood vessels. In the case of the sample that captured (test group), it could be seen that the blood vessels were not loosened and the dye was not out of the blood vessels. From the experimental results, it was confirmed through FIG. 9 that the aNCs_VEGF aptamer effectively captured VEGF, and thus the blood vessels were not loosened. Namely, it is expected that the aNCs_VEGF aptamer can be used as a therapeutic agent for treating macular edema.

INDUSTRIAL APPLICABILITY

A substance causing disease or highly related with disease is set as a target molecule by using the nanoconstructs synthesized according to the present invention, and a corresponding target molecule is captured efficiently and selectively so that disease can be treated or prevented.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for producing dextran polymer-based amplified nucleic acid aptamer nanoconstructs which selectively capture a target molecule, the method comprising the steps of:
   (a) linking an aptamer sequence (Apt) for the target molecule and the DNA sequence of SEQ ID NO: 1 to a dextran polymer, thereby producing a dextran polymer-based DNA aptamer (Dex-DNA-Apt);
   (b) linking an aptamer sequence (Apt) for the target molecule and a sequence complementary to the DNA sequence to the dextran polymer, thereby producing a dextran polymer-based cDNA aptamer (Dex-cDNA-Apt) having a dextran polymer-based cDNA sequence;
   (c) mixing the Dex-DNA-Apt produced in step (a) with the Dex-cDNA-Apt produced in step (b), followed by annealing, thereby producing nanoconstructs (NCs); and
   (d) subjecting the nanoconstructs to rolling circle amplification to amplify the aptamer (Apt), thereby producing nanoconstructs (aNCs) having an amplified aptamer Apt for the target molecule.

2. The method of claim 1, wherein the target molecule is selected from the group consisting of vascular endothelial growth factor (VEGF), bovine serum albumin (BSA), adenosine triphosphate (ATP), hepatitis C virus (HCV) and HIV-1.

3. The method of claim 1, wherein the amplified nanoconstructs have a size of 400 to 1000 nm.

4. Dextran polymer-based amplified nucleic acid aptamer nanoconstructs, produced by the method of claim 1.

5. The dextran polymer-based amplified nucleic acid aptamer nanoconstructs of claim 4, wherein the nucleic acid aptamer is a VEGF-targeting nucleic acid aptamer.

6. A composition for prevention or treatment of cancer, which contains dextran polymer-based amplified VEGF-targeting nucleic acid aptamer nanoconstructs of claim 5 as active ingredients.

7. The composition of claim 6, wherein the prevention or treatment of cancer is performed by allowing the aptamer to bind to vascular endothelial growth factor.

8. A composition for prevention or treatment of macular edema, which contains dextran polymer-based amplified VEGF-targeting nucleic acid aptamer nanoconstructs of claim 5 as active ingredients.

9. The composition of claim 8, wherein the prevention or treatment of macular edema is performed by allowing the aptamer to bind to vascular endothelial growth factor.

* * * * *